United States Patent [19]
Shaffer

[11] Patent Number: 5,688,276
[45] Date of Patent: Nov. 18, 1997

[54] ADJUSTABLE IMPLANT HOLDER INSTRUMENT

[76] Inventor: Benjamin Shaffer, 2111 Wisconsin Ave. NW., Apt. 305, Washington, D.C. 20007

[21] Appl. No.: 502,103

[22] Filed: Jul. 13, 1995

Related U.S. Application Data

[63] Continuation of Ser. No. 83,753, Jun. 23, 1993, abandoned.

[51] Int. Cl.$^6$ ................................................ A61B 17/56
[52] U.S. Cl. ...................... 606/73; 606/79; 606/86; 606/104
[58] Field of Search ................ 606/104, 99, 73, 606/79, 86, 88, 96; 81/44

[56] References Cited

U.S. PATENT DOCUMENTS

| | | | |
|---|---|---|---|
| 2,472,103 | 6/1949 | Giesen . | |
| 2,645,220 | 7/1953 | Gallant et al. | 606/99 |
| 2,765,828 | 10/1956 | Leniz . | |
| 3,316,949 | 5/1967 | Canfield . | |
| 4,631,985 | 12/1986 | Roberts . | |
| 4,667,747 | 5/1987 | Falls et al. | 81/44 |
| 4,704,929 | 11/1987 | Osada . | |
| 5,139,499 | 8/1992 | Small et al. | 606/73 |
| 5,139,520 | 8/1992 | Rosenberg | 623/13 |

*Primary Examiner*—Guy V. Tucker
*Attorney, Agent, or Firm*—Fish & Richardson P.C.

[57] ABSTRACT

An adjustable implant holder instrument having a proximal handle with a movable actuator mechanism. An elongated shaft has a proximal end connected to the proximal handle and has a distal end pivotably interconnected with a holding member which removably carries a surgical implant. A connecting element transfers force, applied to the actuator mechanism, to the holding member to enable selective orientation of the holding member relative to the shaft.

16 Claims, 5 Drawing Sheets

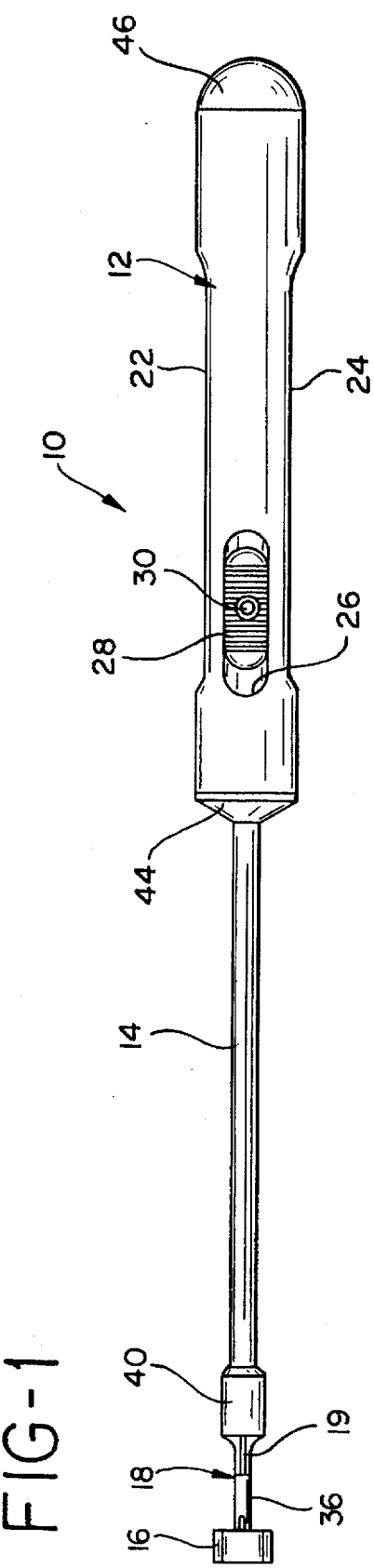
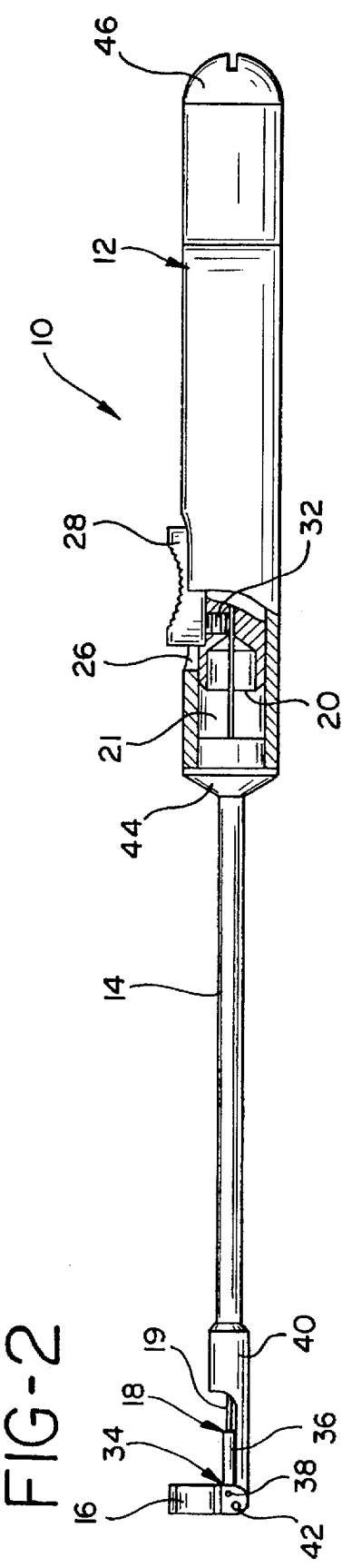

ADJUSTABLE IMPLANT HOLDER INSTRUMENT

This is a continuation of application Ser. No. 08/083,753 filed on Jun. 23, 1993, now abandoned.

FIELD OF THE INVENTION

This invention relates to an instrument for holding an implant and more particularly an instrument which enables remote adjustment of the orientation of the implant relative to the instrument.

BACKGROUND OF THE INVENTION

There are a number of surgical procedures in which an implant such as an interference screw is placed into a bone of a patient. During reconstruction of an anterior cruciate ligament (ACL) using a patellar tendon graft, the graft is harvested having a bone plug at each end of the replacement ligament. One or both plugs are secured within a bone tunnel using an interference screw such as disclosed in U.S. Pat. Nos. 5,139,499 and 5,139,520, incorporated herein by reference.

In one technique of ACL reconstruction using a patellar tendon graft, a portal is made by incision in the soft tissue of the knee, a tunnel is formed in the bone by inserting a drill bit through the portal, a bone plug end of the replacement graft is inserted into the tunnel, and an interference screw is placed through the same portal into the tunnel to secure the bone plug. In some situations, it is difficult to manipulate the screw and driver together through the portal. If the screw becomes dislodged from the driver and drops into the joint, it is a time consuming process to retrieve the screw.

SUMMARY OF THE INVENTION

Therefore, it is an object of the present invention to provide an implant holder instrument which selectively adjusts the orientation of an implant after insertion into a patient.

It is a further object of this invention to provide such an instrument which securely yet removably holds the implant in place until it is connected with a driver.

A still further of this objection is to provide an improved method of placing an implant such as an interference screw into a patient.

This invention features an adjustable implant holder instrument having a proximal handle with a movable actuator mechanism. An elongated shaft has a proximal end connected to the proximal handle and has a distal end pivotably interconnected with a holding member which removably carries a surgical implant. A connecting element transfers force, applied to the actuator mechanism, to the holding member to enable selective orientation of the holding member relative to the shaft.

In one embodiment, the shaft is hollow and the connecting element is a metal rod which travels within the shaft. The holding member is a collar defining a threaded opening through which the implant is spirally insertable. The handle defines a space within it through which the actuating mechanism is longitudinally reciprocatable. The actuating member is a cylinder having an element for releasably engaging the connecting element, and has an actuator element which projects laterally from the cylinder to enable manual actuation of the actuating member.

This invention also features a method of placing an implant into a patient, including forming a first portal in soft tissue of a patient to access a bone of the patient, and providing an adjustable implant holder instrument as described above. The implant is placed into the holding member, a second portal is formed in the soft tissue to intersect the first portal, and the holding member, carrying the implant, is inserted into the second portal. A driver is inserted into the first portal, the implant is aligned with the driver by selectively actuating the actuator mechanism, and the implant is then driven into the bone.

BRIEF DESCRIPTION OF THE DRAWINGS

Other objects, features and advantages will occur from the following description of preferred embodiments and the accompanying drawings, in which:

FIG. 1 is a top plan view of an adjustable implant holder instrument according to the present invention;

FIG. 2 is a side, partial cross-sectional view of the instrument of FIG. 1;

DETAILED DESCRIPTION OF THE DRAWINGS

Figure 3:
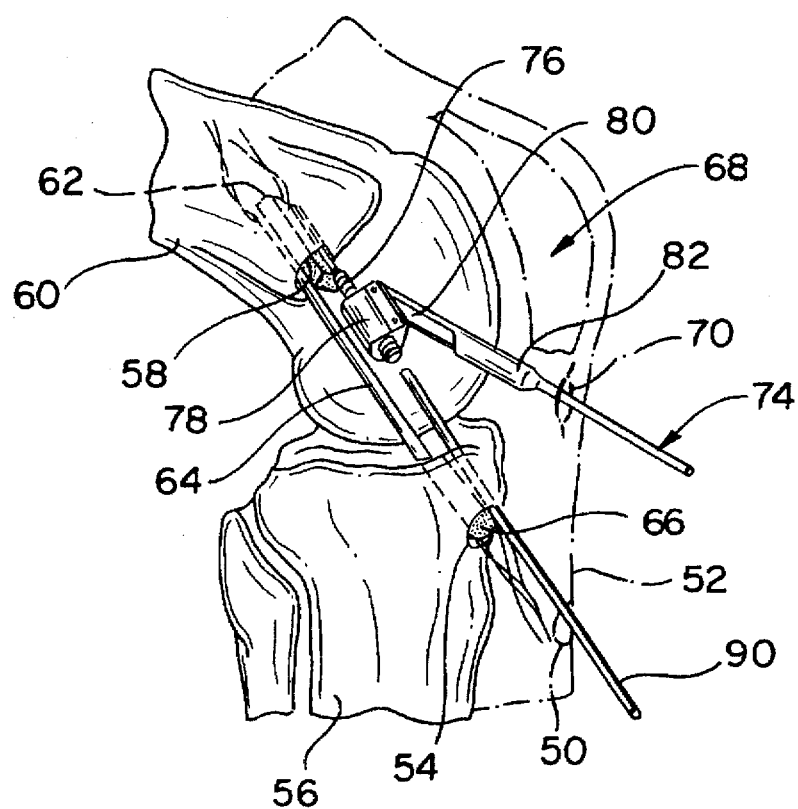
FIG. 3 is a schematic view of an instrument according to the present invention inserted into a knee of a patient together with a patellar tendon graft, an interference screw carried by the instrument, and a driver.

This invention may be accomplished by an instrument having a holding member at its distal end which is pivotably movable relative to the instrument. The holding member has an element, such as threads or fingers, or a resilient lining, for holding an implant such as an interference screw. The instrument facilitates installation of the implant into the holding member, retention of the implant during insertion into a patient, and deployment of the implant into its final position within a patient.

Adjustable screw holder instrument 10, FIGS. 1 and 2, has a proximal handle 12, a hollow shaft 14, a screw holding collar 16, and a connecting mechanism 18 including a rod 19 which is interconnected at its distal end with the collar 16 and at is proximal end with an actuating member 20. The actuating member 20 is a cylinder which reciprocates within a space 21 within handle 12. The handle 12 further defines recesses 22 and 24 to facilitate gripping of the handle 12 by the fingers of a hand, and defines an upper opening 26 through which a sliding actuating element 28 projects. The element 28 is attached by a cap screw 30 to the cylinder 20. The proximal end of the connecting rod 19 is engaged by a separate setscrew 32. The cylinder 20 preferably is coated with a substance having a low coefficient of friction such as synthetic resin polymers under the trade marks TEFLON or SILVERSTONE.

The proximal end of connecting mechanism 18 includes a pivot assembly 34 having a rectangular bar 36 with opposing distal tangs 38 which engage the screw holding collar 16. The rod 19 of connecting mechanism 18 is soldered to the rectangular piece 36. The screw holding collar 16 is connected to a support 40 by a pivot pin 42 such as a metal dowel. The support 40 is soldered or welded to the tube 14 which, in turn, is soldered to a conical adapter 44 that is welded to the handle 12. Proximal end cap 46 is threadably attached to the proximal end of the handle 12.

In one construction, the handle 12 is manufactured from a 4.20 inch length of 303 stainless steel rod having an outer diameter of 0.62 inch, as are the material and outer diameter of adapter 44 and end cap 46. The cylinder 20 is 303 stainless steel rod having an outer diameter of 0.415 inch and a length of 1.3 inch, the actuator element 28 is machined from an aluminum ⅜ inch by ⅜ inch bar having a length of 0.75 inch, the rod 19 has an outer diameter of 0.31 inch, a length of 6 inches, and is made of 17-4 stainless steel. The support tube 14 is 420B stainless steel tube having an outer diameter of 0.224 inch, an inner diameter of 0.67 inch, and a length of 4 inches. The support 40 is manufactured of 17-4 pre-hardened stainless steel having an outer diameter of 0.25 inch and a length of 1.31 inch, and rectangular bar 36 is made of 17-4 pre-hardened stainless steel having a width of 0.09 inch, a height of 0.06 inch, and a length of 0.56 inch. The screw holding collar 16 is formed of 17-4 pre-hardened stainless steel, has an outer diameter of 0.626 inch with an internal thread having the same pitch as an interference screw to be carried by the collar 16, and has a length of 0.84 inch.

One use of an adjustable implant holder instrument according to the present invention is described as follows. During ACL reconstruction, a first portal 50 is made in soft tissue 52, and a tunnel 54 is made in a tibia 56 of a patient such as described in U.S. Pat. No. 5,139,520. A tunnel 58 is then formed in a femur 60, and a bone block 62 of a patellar tendon graft 64 is inserted within the femoral tunnel 58. A bone block 66 rests within the tibial tunnel 54. An arthroscope, not shown, is used to observe procedures conducted within the capsular region of the knee joint 68.

A second, anteromedial portal 70 is formed in the soft tissue 52, and an adjustable holder instrument 74 is inserted through the second portal 70. An interference screw 76, which previously has been threadably inserted into a holding collar 78, is aligned with the femoral tunnel 58 by manipulating pull wire 80 which changes the orientation of the holder 78 relative to a support 82.

Figure 4:
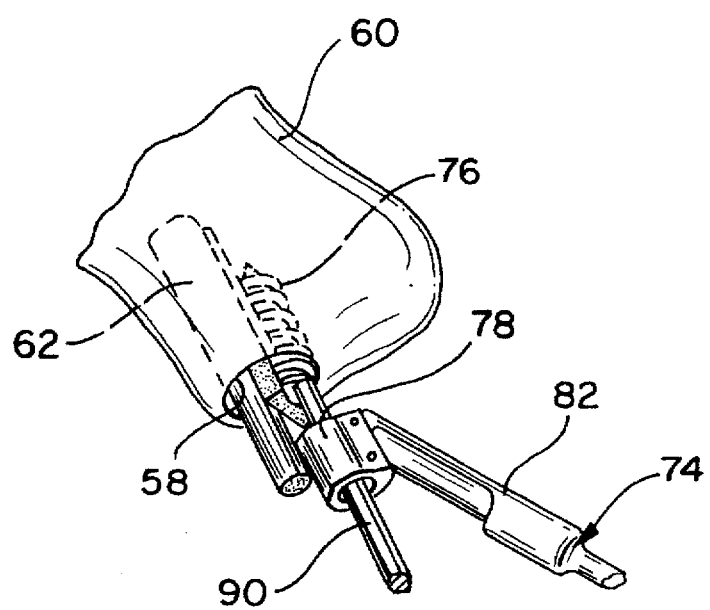
FIG. 4 is a schematic view of a portion of FIG. 3 after the driver has rotatably driven the screw out of the instrument and into the bone tunnel.
Figure 5:
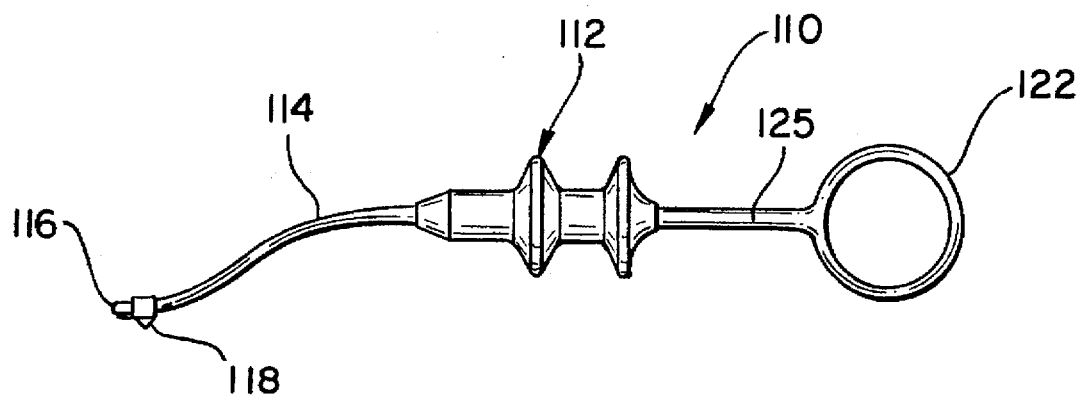
FIG. 5 is a schematic side view of a novel intra-articular measuring device.
Figure 6:
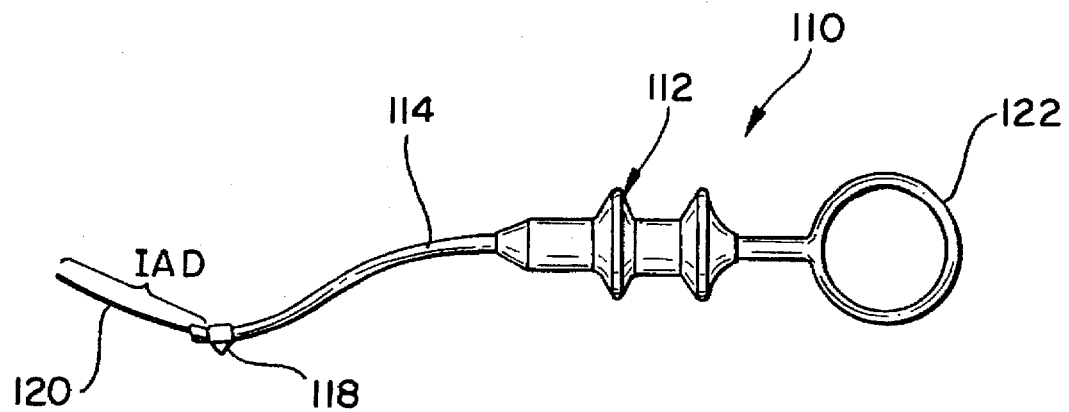
FIG. 6 shows the device of FIG. 5 with the measurement probe extended over an intra-articular distance IAD.
Figure 7:
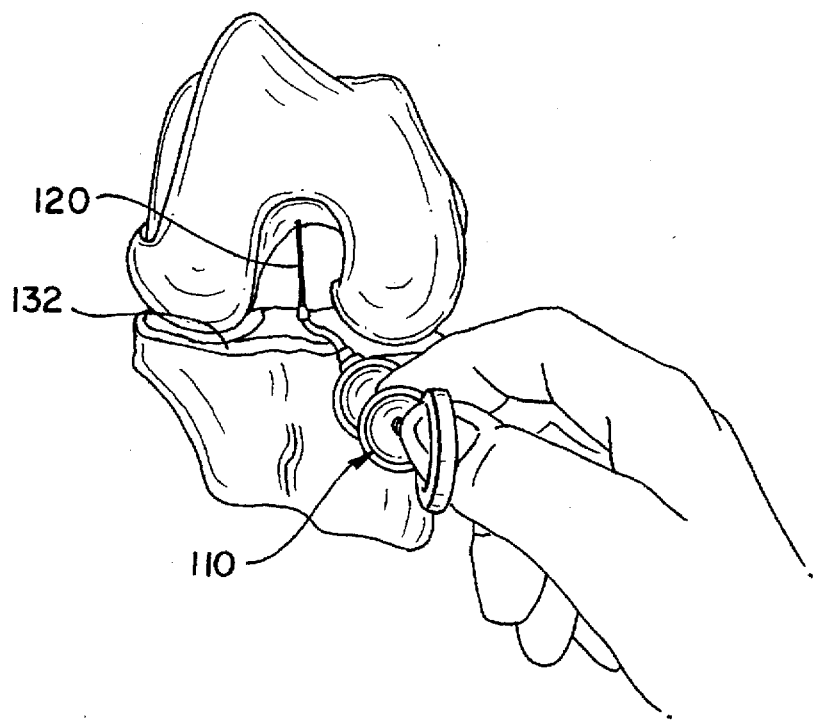
FIG. 7 is a schematic perspective view of the intra-articular device of FIGS. 5 and 6 being used within a knee joint.

After proper orientation of the screw 76 is achieved as determined arthroscopically, a driver 90 is inserted through the first portal 50 and is engaged with the proximal end of the screw 76. The driver 90 is rotated to spirally drive the screw 76 into the femoral tunnel 58 as shown in FIG. 4.

Figure 8:
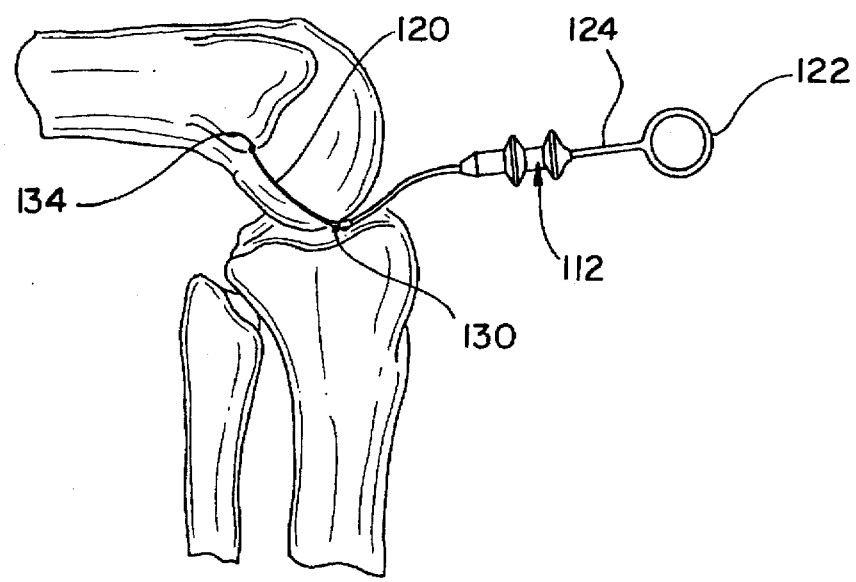
FIG. 8 is a schematic side view illustrating measurement of the distance IAD.
Figure 8A:
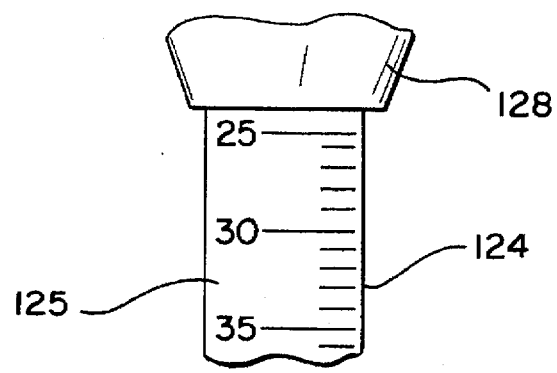
FIG. 8A is an enlarged view of FIG. 8.

Preferably, the actual length of the ligament to be replaced is measured using a novel intra-articular measuring device 110, FIGS. 5–8, having a handle 112 connected to a hollow tube 114 which terminates in a distal opening 116. A projection 118 is seated on the tibial plateau as described below. A probe 120 is advanceable beyond the opening 116 when finger loop 122 is advanced towards the handle 112. A gauge 124 on shaft 125 indicates the extension length of the probe 120, as shown in an enlarged view in FIG. 8A.

In one construction, the handle 112 has a length of approximately 2.6 inch and the tube 114 projects approximately five inches distally beyond it. The probe 120 is 5.5 inch in length, and the finger loop 122 and the shaft 125 have a combined length of 3.1 inch. The gauge 124 carries markings at one mm increments between between 0 to 45 mm.

During use, the intra-articular measurement device 110 is inserted through the anteromedial portal 70, FIG. 3, until the projection 118 is seated at tibial insertion point 130 on the tibial plateau 132. The probe 120 is advanced thereafter until the femoral insertion point 134 is reached. To thereby read the exact intra-articular distance IAD between point 130 and point 134.

During a study of thirty-four bone-patellar tendon-bone autograph endoscopic ACL reconstructions, the intra-articular distance IAD was found to range from 21 mm to 33 mm, with the average being 26.3±3.0 mm. The novel intra-articular measuring device enables precise measurement of the distances to properly place a replacement ligament within the femoral and tibial tunnels.

Figure 9:
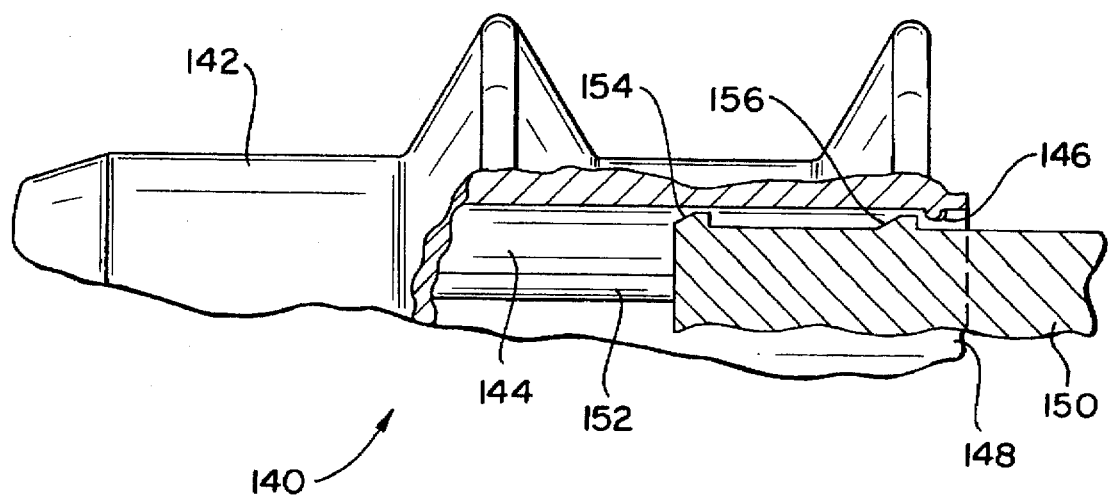
FIG. 9 is a partial cross-sectional top view of an alternative intra-articular device.

An improved intra-articular measuring device 140, FIG. 9, has a handle 142 which defines a passageway 144 and a proximal ridge 146 on either side of a proximal opening 148. A slideable shaft 150 is attached at its distal end to a probe 152 and defines ribs 154, 156 on either side. The ridge 146 and ribs 154, 156 enhance stability during movement of the shaft 150 relative to the handle 142, serve to center shaft 150, and act as a stop members to inhibit inadvertent withdrawal of the shaft 150. In one construction, the ribs 154, 156 have a height of 0.007 to 0.008 inch, a length of 0.030 inch, and a distal edge tapered at thirty degrees. Ridge 146 has a height of 0.006 inch.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. An adjustable holder instrument comprising:

a proximal handle having a moveable actuating member;

an elongated shaft having a proximal end connected to said proximal handle and having a distal end;

threaded holding means for removably carrying a surgical interference screw, said holding means including a collar defining a threaded opening through which the screw is spirally insertable;

pivot means for pivotably interconnecting said holding means with said distal end of said shaft;

means, connecting said actuating member to said holding means, for transferring force, applied to said actuating member, to said holding means to enable selective orientation of said holding means relative to said shaft; and wherein said shaft is hollow and said means for transferring force travels within said shaft.

2. The holder instrument of claim 1 wherein said connecting means is a metal rod.

3. The holder instrument of claim 2 wherein said handle defines a space within it through which said actuating member is longitudinally reciprocatable.

4. The holder instrument of claim 3 Wherein said actuating member is a cylinder having means for releasably engaging said metal rod, and having an actuator element which projects laterally therefrom to enable manual actuation of said actuating member.

5. A method of placing an implant into a patient, comprising:

forming a first portal in soft tissue of a patient to access a bone of the patient;

providing an adjustable implant holder instrument including:

a proximal handle having a moveable actuating member;

an elongated shaft having a proximal end connected to the proximal handle and having a distal end;

threaded holding means for removably carrying a surgical implant;

pivot means for pivotably interconnecting the holding member with the distal end of the shaft; and means, connecting the actuating member to the holding means, for transferring force, applied to the actuating member, to the holding means to enable selective orientation of the holding means relative to the shaft;

placing an implant into the holding means so that the implant is removably carried by the holding means;

forming a second portal in the soft tissue intersecting the first portal;

inserting the holding means, carrying the implant, into the second portal;

inserting a driver into the first portal;

aligning the implant with the driver into the first portal;

aligning the implant with the driver by selectively actuating the actuating member; and driving the implant into the bone.

6. The method of claim 5 further including the step of forming a hole in the bone after the step of forming the first portal, and the driving step includes driving the implant into the hole formed in the bone.

7. The method of claim 6 wherein the implant is an interference screw.

8. The method of claim 7 wherein the first and second portals are formed in a knee joint.

9. An adjustable implant holder instrument comprising:

a proximal handle having a moveable actuating member;

an elongated shaft having a proximal end connected to said proximal handle and having a distal end;

a threaded collar which is capable of removably carrying a surgical implant, said collar defining a threaded opening through which the implant is spirally insertable;

pivot means for pivotably interconnecting said holding member with said distal end of said shaft; and means, connecting said actuating member to said collar, for transferring force, applied to said actuating member, to said collar to enable selective orientation of said collar relative to said shaft.

10. The holder instrument of claim 9 wheretin said shaft is hollow and said means for transferring movably extends within said shaft.

11. The holder instrument of claim 10 wherein said means for transferring is a metal rod.

12. The holder instrument of claim 10 wherein said handle defines a space within it through which said actuating member is longitudinally reciprocatable.

13. An adjustable implant holder instrument comprising:

a proximal handle having a moveable actuating member, said handle defining a space within it through which said actuating member is longitudinally reciprocatable;

an elongated shaft having a proximal end connected to said proximal handle and having a distal end;

holding means for removably carrying a surgical implant;

pivot means for pivotably interconnecting said holding member with said distal end of said shaft;

means, connecting said actuating member to said holding means, for transferring force, applied to said actuating member, to said holding means to enable selective orientation of said holding means relative to said shaft; and said actuating member being a cylinder having means for releasably engaging said connecting means, and having an actuating element which projects laterally therefrom to enable manual actuation of said actuating member.

14. The holder instrument of claim 13 wherein said shaft is hollow and said means for transferring movably extends within said shaft.

15. The holder instrument of claim 14 wherein said means for transferring is a metal rod.

16. The holder instrument of claim 14 wherein said holding means is a collar defining a threaded opening through which the implant is spirally insertable.

* * * * *

UNITED STATES PATENT AND TRADEMARK OFFICE
CERTIFICATE OF CORRECTION

PATENT NO.   : 5,688,276

DATED        : November 18, 1997

INVENTOR(S)  : Benjamin Shaffer

It is certified that error appears in the above-identified patent and that said Letters Patent is hereby corrected as shown below:

Col. 4, claim 1, line 38, after "adjustable" insert
--screw--.

Col. 4, claim 4, line 61, replace "Wherein" with --wherein--

Signed and Sealed this

Twenty-first Day of April, 1998

Attest:

BRUCE LEHMAN

*Attesting Officer*             *Commissioner of Patents and Trademarks*